United States Patent [19]

Koyama

[11] Patent Number: 4,638,146
[45] Date of Patent: Jan. 20, 1987

[54] METHOD OF PROTECTING EYES FROM WELDING RAYS IN ARC WELDING AND APPARATUS THEREFOR

[75] Inventor: Ario Koyama, Tokyo, Japan

[73] Assignees: Nagase Sangyo Kabushiki Kaisha; Kabushiki Kaisha Sensor Gijutsu Kenkyujo, both of Japan

[21] Appl. No.: 785,588

[22] Filed: Oct. 8, 1985

[30] Foreign Application Priority Data

Oct. 16, 1984 [JP] Japan ................................ 59-216976

[51] Int. Cl.$^4$ .............................................. B23K 9/32
[52] U.S. Cl. ...................................... 219/147; 219/132
[58] Field of Search .......................... 219/147, 132, 136

[56] References Cited

U.S. PATENT DOCUMENTS 3,873,804  3/1975  Gordon ............................... 219/147
4,410,789  10/1983  Story .................................. 219/132

FOREIGN PATENT DOCUMENTS 230805  1/1944  Switzerland ........................ 219/147

Primary Examiner—Clifford C. Shaw
Attorney, Agent, or Firm—Steinberg & Raskin

[57] ABSTRACT

A method of protecting eyes from welding rays in arc welding and an apparatus therefor are disclosed which are capable of closing a filter plate over a period from right before the generation of arc welding rays to the termination of the generation to fully intercept the rays, to thereby effectively protect the eyes of an operator from the rays. The invention is constructed in a manner such that a controller carries out the on-off control of a voltage applied from a filter power source to a PLZT filter plate depending upon a signal supplied from a detection circuit thereto when the detection circuit detects a built-up current occurring in a welding current, to thereby carry out the actuation of the filter plate.

14 Claims, 7 Drawing Figures

METHOD OF PROTECTING EYES FROM WELDING RAYS IN ARC WELDING AND APPARATUS THEREFOR

BACKGROUND OF THE INVENTION

1. Field of the Invention

This invention relates to a method of protecting eyes from welding rays in arc welding and an apparatus therefor, and more particularly to such eye-protecting method and apparatus which are adapted to utilize a light-intercepting mask or personal eye-protector for welding having a filter plate formed of a material exhibiting an electro-optic effect arranged thereon.

2. Description of the Prior Art

Conventionally, a personal eye-protector or light-intercepting mask for welding has been widely used to prevent welding rays from entering the eyes of an operator in arc welding. The conventional personal eye-protector often includes a light-intercepting filter plate formed of an electro-optic material. The personal eye-protector of such a type is adapted to keep the filter plate light-permeable to form a bright field until a welding electrode mounted on an electrode holder is contacted with the portion of works to be subjected to welding to generate arc welding rays, and detect the arc welding rays to cause the filter plate to extinguish the welding rays passing therethrough to form a dark field after the welding rays are generated. Such actuation of the filter plate is controlled in a manner such that a light receptor detects arc welding rays to generate a detection signal, which carries out the on-off control of a voltage applied to the filter plate formed of a material exhibiting an electro-optic effect such as, for example, (Pa, La)(Zr, Ti)O which is an optically transparent electro-optic ceramic material (hereinafter referred to as "PLZT"), liquid crystal or the like.

Such a material as PLZT or the like indeed effectively intercepts arc welding rays; however, it causes a response delay which corresponds the sum of response time of an element level and response time of a circuit system over a period from the on-off control of the voltage to the exhibition of function as an optical shutter, during which it fails to intercept arc welding rays and therefore prevent arc welding rays from entering eyes of an operator.

In arc welding operation, as shown in FIG. 1, arc welding rays are generated with rapid rising, resulting in the conventional personal eye-protector or light-intercepting mask constructed as described above failing to prevent a large amount of arc rays from entering the eyes of an operator. More particularly, unfortunately, a light receptor is not adapted to detect arc welding rays at the same time of the generation. Instead, it is adapted to start the actuation when arc welding rays reach a threshold level $q_1$ to generate an output signal. This is for the purpose of blocking noise due to the sunlight or illumination. Accordingly, arc welding rays increase in amount to a level indicated by $q_2$ in FIG. 1 when it comes time ($t_1$) for the filter plate to close, resulting in substantially all the rays generated by the time passing through the filter plate without being extinguished.

This causes an operator to suffer from electric ophthalmia due to inflammation on the horny coat or conjunctiva of an eye, because arc welding rays contain a large amount of ultraviolet rays. Further, this causes eye trouble such as muddiness of the crystalline lens or the like due to the exposure to infrared rays contained in arc welding rays for a long period of time.

SUMMARY OF THE INVENTION

The present invention has been made in view of the foregoing disadvantage of the prior art.

Accordingly, it is an object of the present invention to provide a method of protecting eyes from welding rays in arc welding which is capable of closing a filter plate over a period from right before the generation of arc welding rays to the termination of the generation to fully intercept arc welding rays from eyes.

It is another object of the present invention to provide a method of protecting eyes from welding rays in arc welding which is capable of carrying out the on-off control of a filter plate without connecting a personal eye-protector or eye-protecting mask to an electric circuit for welding, to thereby significantly improve the workability.

It is a further object of the present invention to provide a method of protecting eyes from welding rays in arc welding which is capable of carrying out the on-off control of a filter plate without malfunction.

It is a further object of the present invention to provide an eye-protecting apparatus for arc welding which is capable of closing a filter plate over a period from right before the generation of arc welding rays to the termination of the generation to fully protect eyes from arc welding rays.

It is a still further object of the present invention to provide an eye-protecting apparatus for arc welding which is capable of carrying out the on-off control of a filter plate without connecting a personal eye-protector or eye-protecting mask to an electric circuit for welding, to thereby significantly improve the workability.

It is still another object of the present invention to provide an eye-protecting apparatus for arc welding which is capable of carrying out the on-off control of a filter plate without malfunction.

It is yet another object of the present invention to provide an eye-protecting apparatus for arc welding which is inexpensive and compact in structure.

In accordance with one aspect of the present invention, there is provided a method of protecting eyes from welding rays in arc welding which utilizes a personal eye-protector having a filter plate arranged thereon, comprising the steps of detecting the occurrence of a transient built-up current in a welding current to generate a detection signal; and controlling a voltage applied to the filter plate depending upon the detection signal.

In a preferred embodiment of the present invention, the filter plate is formed of PLZT material.

In a preferred embodiment of the present invention, the detection of occurrence of the transient built-up current is carried out by detecting a magnetic field generated around a welding current cable.

In a preferred embodiment of the present invention, the occurrence of the magnetic field is detected at the position of an electrode holder, and the detection signal is converted into a light signal or wave signal of a predetermined frequency and received at the position of the eye-protector.

Alternatively, the occurrence of the magnetic field may be detected at the position of the eye-protector.

In accordance with another aspect of the present invention, there is provided an eye-protecting apparatus for arc welding comprising a filter plate for an eye-protector, the filter plate being formed of a material which is capable of exhibiting an electro-optic effect; a source circuit for generating a voltage applied to the filter plate; a detection circuit for detecting a transient built-up current in a welding current; and a controller for controlling the voltage applied to the filter plate depending upon a signal supplied from the detector.

In a preferred embodiment of the present invention, the detection circuit comprises a magnetic field detector; a transmitter for transmitting a plurality of signals different in frequency from each other depending upon signals supplied from the magnetic field detector thereto; a receiver for receiving the signals supplied from the transmitter; and a frequency discriminator for discriminating the frequencies of the signals received by the receiver.

In a preferred embodiment of the present invention, the magnetic field detector and transmitter are arranged on an electrode holder; and the frequency discriminator, the source circuit for the filter plate and the contoller are arranged on the eye-protector.

In a preferred embodiment of the present invention, the filter plate is formed of a PLZT material.

In another preferred embodiment, the detection circuit comprises a magnetic field detector; an operational amplifier including a low-pass filter; and a comparator including a threshold level setting means.

In the embodiment, the source circuit, detection circuit and controller are arranged on an eye-protector.

BRIEF DESCRIPTION OF THE DRAWINGS

These and other objects and many of the attendant advantages of the present invention will be readily appreciated as the same becomes better understood by reference to the following detailed description when considered in connection with the accompanying drawings in which like reference characters designate like or corresponding parts throughout, wherein.

DETAILED DESCRIPTION OF THE PREFERRED EMBODIMENT

Now, a method of protecting eyes from welding rays in arc welding and an apparatus therefor according to the present invention will be described hereinafter with reference to the accompanying drawings.

FIGS. 2 to 5 illustrate a first embodiment of an apparatus for protecting eyes from welding rays in arc welding according to the present invention.

Figure 1:
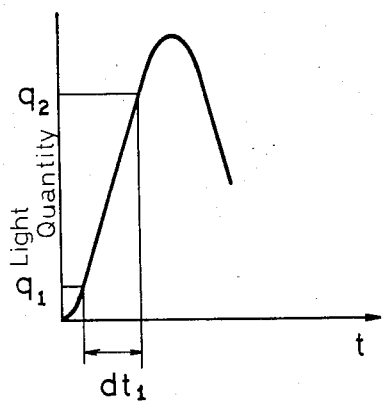
FIG. 1 is a graphical representation showing the rising characteristics of quantity of arc welding rays.
Figure 2:
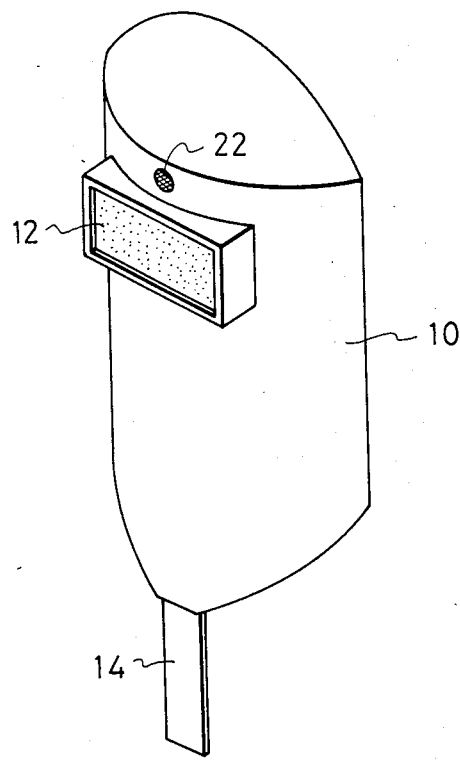
FIG. 2 is a front perspective view showing an example of a light-intercepting mask or personal eye-protector for welding which is adapted to be used in a first embodiment of an eye-protecting apparatus for arc welding according to the present invention.
Figure 3:
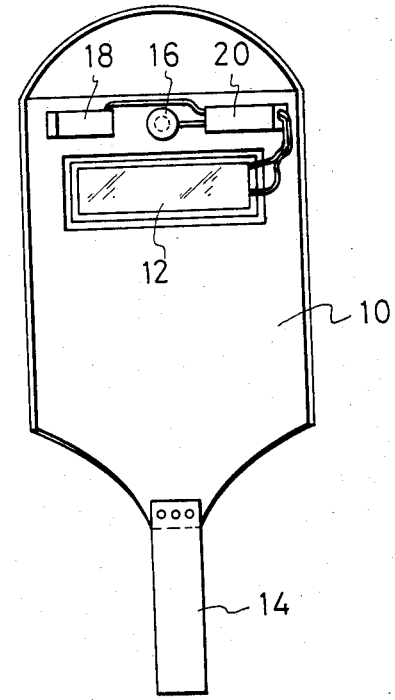
FIG. 3 is a rear elevation view of the eye-protector shown in FIG. 1.

FIGS. 2 and 3 show an example of a light-intercepting mask or personal eye-protector for welding which is adapted to be used in the first embodiment. In FIGS. 2 and 3, the eye-protector is generally designated by reference numeral 10. The illustrated eye-protector 10, as shown in FIG. 2, includes a light-intercepting filter plate 12 formed of a PLZT material and a grip 14. Also, the eye-protector 10, as shown in FIG. 3, includes a light receptor 16, a battery casing 18 for receiving therein battery means for circuit elements such as a receiver, a frequency discriminator, a controller and a filter power source described in detail hereinafter, and a circuit casing 20 for receiving therein the circuit elements, which each are mounted on the upper portion of the rear surface of the eye-protector 10. The light receptor 16 has a light-receiving element 22 (FIG. 2) exposedly mounted on the front surface of the eye-protector 10.

Figure 4:
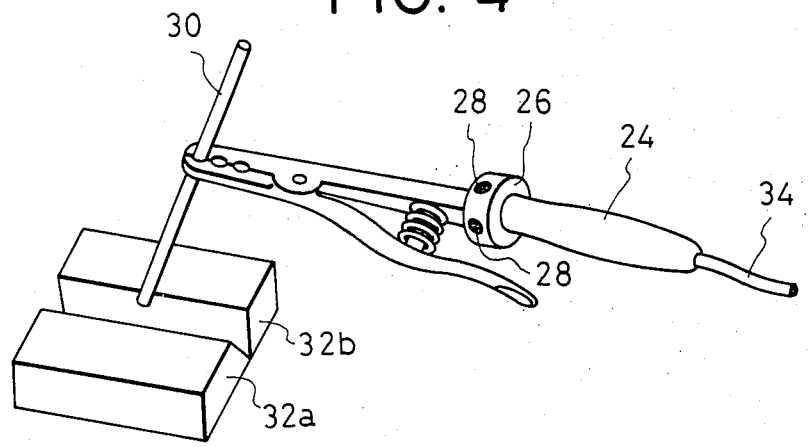
FIG. 4 is a perspective view showing the welding portion of the first embodiment of the present invention.

FIG. 4 shows an arc welding section of the illustrated embodiment, wherein reference numeral 24 designates an electrode holder and 26 designates a detecting section casing which is mounted in position on the electrode holder 24 and adapted to receive therein a magnetic field detector and a transmitter described hereinafter. The casing 26 is provided on the periphery thereof with at least one light emitting element 28 for a light emitter described hereinafter. Reference numeral 30 indicates a welding electrode, reference numerals 32a and 32b each designate a work to be subjected to arc welding, and 34 designates a power cable or welding current cable for supplying an electric current to the welding electrode 30.

Figure 5:
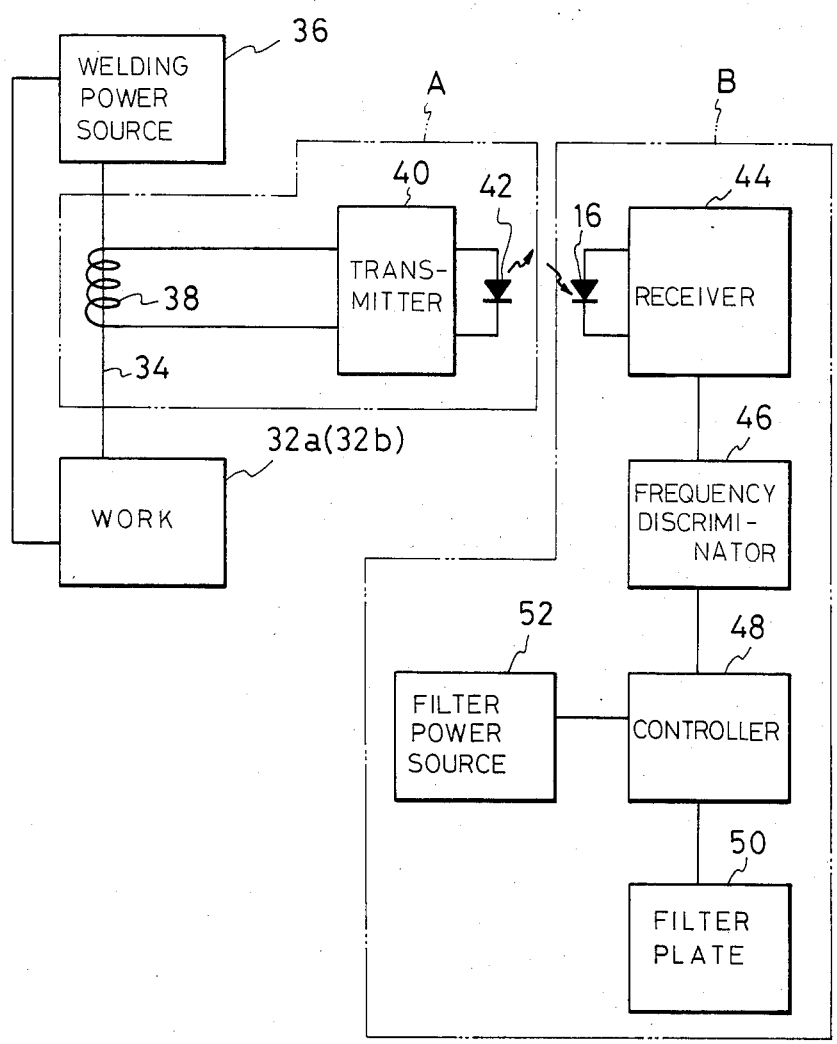
FIG. 5 is a block circuit diagram showing an example of an electric circuit which is adapted to be used in the first embodiment of the present invention.

FIG. 5 shows an example of an electric circuit adapted to be used in the first embodiment illustrated. In FIG. 5, reference numeral 36 designates a welding power source for an AC welder which serves to supply a welding current to the welding electrode 30 and works 32a and 32b through the power cable 34. 38 indicates a magnetic field detector for detecting the flow of a welding current through the power cable 34, which comprises a coil wound through an insulator (not shown) on the periphery of the power cable 34 and is received in the detecting section casing 26. Connected to the magnetic field detector 38 is a transmitter 40 which is adapted to receive a signal supplied from the magnetic field detector 38 to generate a signal of a predetermined frequency. To the transmitter 40 is connected a light emitter 42 which is controlled by a signal supplied from the transmitter 40 to emit a light signal of a predetermined frequency. In the embodiment illustrated, the light emitter 42 comprises an infrared light emitting diode.

In the embodiment illustrated, a circuit section comprising the above-described magnetic field detector 38, transmitter 40 and light emitter 42 and enclosed by two-dot chain lines A in FIG. 5 are received in the detecting section casing 26 of the eye-protector 10. Alternatively, the circuit section A may be received in the electrode holder 24.

The circuit used in the illustrated embodiment also includes a circuit section enclosed by two-dot chain lines B in FIG. 5, which is also disposed on the rear surface of the eye-protector 10. The circuit section B comprises an infrared light receiving diode acting as the light receptor 16, a receiver 44 connected to the light receptor 16 to operate and amplify an input signal supplied from the light receptor 16, a frequency discriminator 46 connected to the receiver 44, a controller 48 connected to the frequency discriminator 46, a filter plate 50 formed of a PLZT material which is connected to one of output terminals of the controller 48, and a filter power source 52 for the PLZT filter plate 50 which is connected to the other output terminal of the controller 48. The controller 48 serves to carry out the on-off control of the filter power source depending upon a signal supplied from the frequency discriminator thereto, to thereby control a voltage applied from the filter power source 52 to the PLZT filter plate 50.

In the illustrated embodiment, the above-described magnetic field detector 38, transmitter 40, light emitter 42, light receptor 16, receiver 44 and frequency discriminator 46 constitute a detection circuit.

Also, in the illustrated embodiment, as described above, the magnetic field detector 38 comprising the coil is used for detecting the flow of a current through the power cable 34. However, any other suitable means may be used for the detection. Further, any other light emitting element and light receiving element may be substituted for the infrared light emitting diode 42 and infrared light receiving diode 16, respectively. Furthermore, a radio wave may be used as sending means from the transmitter 40 to the receiver 44.

The frequency discriminator 46 serves to discriminate a frequency of an output signal of the transmitter 40. Any conventional circuit may be used for the frequency discriminator 46. The filter plate 50 formed of an optically transparent electro-optic ceramic material (Pa, La)(Zr, Ti)O has an electrode (not shown) arranged therein; so that it may constitute an optical shutter in combination with another deflection plate, because the polarization occurs therein to change the direction of polarization of light passing therethrough when a voltage is applied thereto.

However, in the illustrated embodiment, any other material such as, for example, PZT, liquid crystal or the like which is capable of exhibiting an electro-optic effect may be used for the filter plate 24.

Now, the manner or method of intercepting welding rays or protecting eyes from welding rays in arc welding will be described hereinafter with reference to FIGS. 2 to 6.

First, the welding electrode 30 is contacted with the works 32a and 32b and a welding current is supplied to the welding electrode 30 through the welding current cable 34 from the welding power source 36. Then, the welding electrode 30 is spaced by a short distance from the works 32a and 32b to generate arc discharge between the welding electrode 30 and the works 32a and 32b. At this time, a transient built-up current is generated in the welding current right before the generation of arc welding rays.

Then, the transmitter 40 actuates to cause the light emitter or infrared light emitting diode 42 to generate an infrared light signal having a frequency of 50 kHz when the value of an electric current detected by the coil 38 is zero; whereas when the coil 38 detects the above-described transient built-up current, the transmitter 40 causes the diode 42 to generate an infrared light signal having a frequency of, for example, 38.4 kHz other than that of 50 kHz and subsequently continue generation of the light during the arc discharge.

The so-generated infrared light signal is received by the light receptor or infrared light receiving diode 16, operated and amplified by the receiver 44, and then supplied to the frequency discriminator 46. The frequency discriminator 46 discriminates whether the frequency of the signal input thereto is 50 kHz or 38.4 kHz and supplies the so-discriminated signal to the controller 48. The controller 48 then carries out the on-off control of a voltage applied from the filter power source 52 to the PLZT filter plate 50 depending upon the signal supplied from the frequency discriminator 46 thereto.

Figure 6:
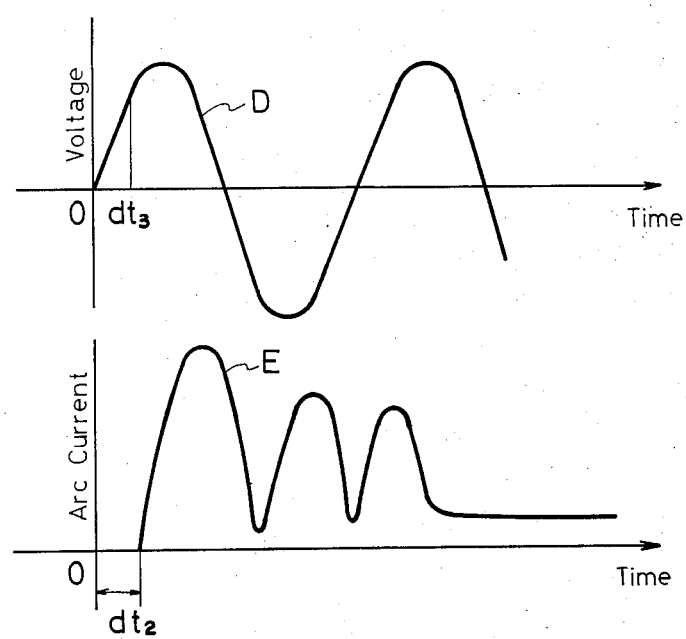
FIG. 6 is a graphical representation showing the relationships between a welding current and arc discharge.

More particularly, the controller 48 carries out the on-control of a voltage applied to the PLZT filter plate 50 to open a shutter to form a bright field when a welding current is not flowing through the power cable 34 and the frequency of the signal output from the transmitter 40 is 50 kHz; whereas when the frequency of the signal is 38.4 kHz over a period from the the start of flow of a welding current through the power cable to the arc discharge, it carries out the off-control of the voltage to close the shutter to form a dark field. In this instance, as shown in FIG. 6, a delay time $dt_2$ is required from the occurrence of a transient built-up current in a welding current D to the occurrence of arc discharge E. Thus, there is a response time $dt_3$ from the detection of occurrence of the transient built-up current to the discharge of charge accumulated in the PLZT filter plate 50 which is the sum of a response time of an element level of the PLZT filter plate 50 and a response time of the circuit system. However, the response time $dt_3$ is within the range of the above-described delay time $dt_2$, so that the PLZT filter plate 50 may serve as an optical shutter right before the occurrence of arc welding rays to completely accomplish the protection of eyes from the arc rays. In the illustrated embodiment, the controller 48 is preferably constructed to cause the PLZT filter plate 50 to be closed for the sake of safety when neither the frequency of 50 kHz nor that of 38.4 kHz is detected by the frequency discriminator 46.

In the illustrated embodiment, 50 kHz and 38.4 kHz are illustratively used for frequencies to be discriminated at the frequency discriminator 46. However, it is of course that the embodiment is not limited to the use of such frequencies.

Figure 7:
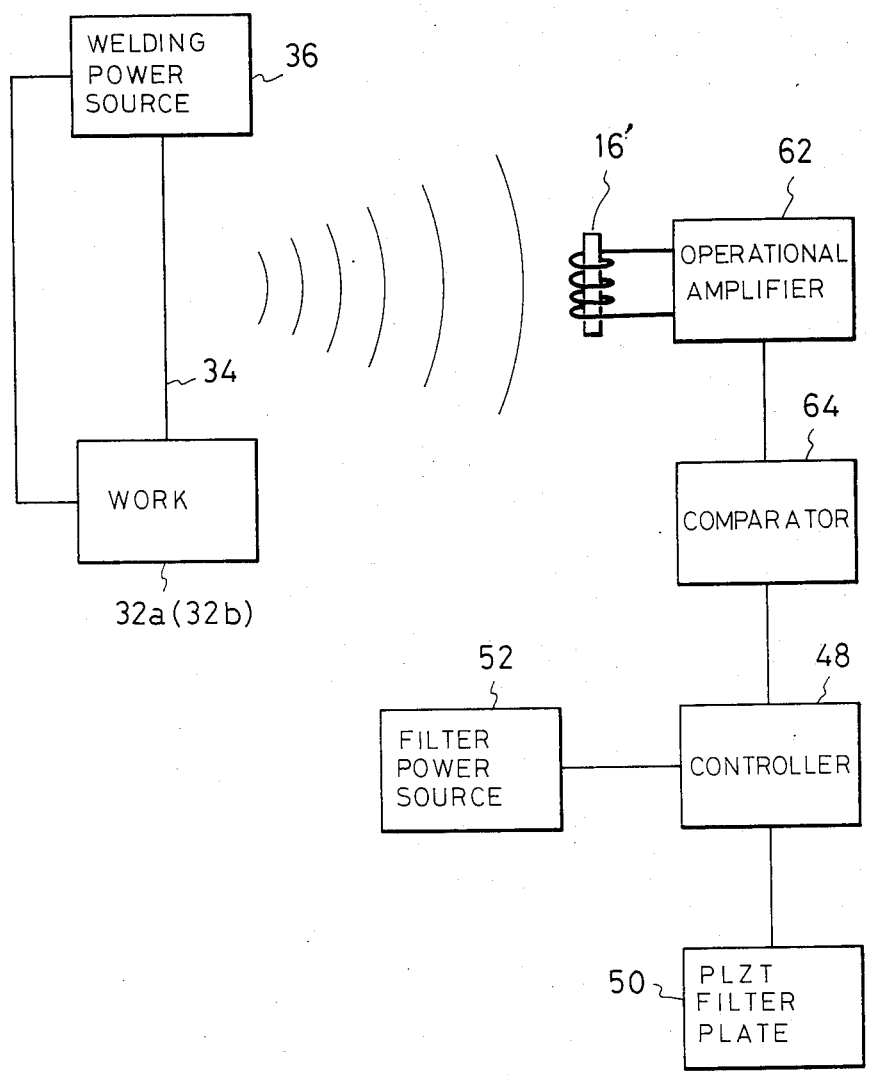
FIG. 7 is a block circuit diagram showing an electric circuit for a second embodiment of an eye-protecting apparatus for arc welding according to the present invention.

FIG. 7 shows an electric circuit in a second embodiment of a light-intercepting apparatus or eye protecting apparatus for arc welding according to the present invention. The second embodiment is adapted to detect, by means of a magnetic field detector arranged on an eye-protector, a magnetic field generated due to the flowing of a welding current through a power cable.

In FIG. 7, reference numeral 16' designates a magnetic field detector comprising a cored coil which is substituted for the light receptor 16 in the first embodiment described above. The detector 16' is fixedly mounted on an eye-protector (not shown) constructed in substantially the same manner as that shown in FIG. 3. Also, it may be arranged at a position corresponding to the light receptor 20 in the first embodiment. Connected to the magnetic field detector 16' is an operational amplifier 62 which includes a low-pass filter. The operational amplifier 62 acts to amplify a voltage induced at the magnetic field detector 16', and remove, as a noise component, the portion of the induced voltage which has a frequency above that of the power source by means of the low pass filter and supply the voltage portion to a comparator 64 connected to the output terminal of the amplifier 62.

The comparator 64 contains therein a threshold setting circuit and serves to adjust a magnetic field detecting level depending upon a welding current to set a signal-to-noise ratio (S/N). The output from the comparator 64 is supplied in the form of a shutter open signal or shutter close signal which is an analog or digital signal. In the embodiment, the low-pass filter incorporated in the operational amplifier 62 has a frequency set to coincide with the frequency of a welding current which is typically supplied from a commercial AC power source of 50 Hz or 60 Hz.

The circuit also includes a controller 48 which is connected to the output terminal of the comparator 64 to receive the signal output from the comparator 64. When the shutter open signal is supplied to the controller 48, the controller is adapted to carry out the on-control of a voltage applied from a filter power source 52 connected to one output terminal thereof to a PLZT filter plate 50 connected to the other output terminal thereof; whereas the supply of the shutter close signal thereto causes it to carry out the off-control of the voltage.

The remaining part of the second embodiment is constructed in substantially the same manner as the first one described above.

Now, the manner of operation of the second embodiment will be described hereinafter with reference to FIG. 7.

When a welding current is not flowing through a power cable 34, the shutter open signal is constantly supplied from the comparator 64 to the controller 48, which carries out the on-control of a voltage applied to the PLZT filter plate 50 as described above, resulting in the PLZT filter plate 50 being optically opened to form a bright field. On the contrary, when a transient built-up current is flowed through the welding current cable 34 to cause a magnetic field to be generated around the cable 34, the flow of a current through the coil of the magnetic field detector 16' momentarily occurs to cause the shutter close signal to be supplied from the comparator 64 to the controller 48, so that the controller may carry out the off-control of a voltage applied from the filter power source 52 to the PLZT filter plate 50. This results in the PLZT filter plate 50 being optically closed to form a dark field. Thus, it will be noted that the filter plate 50 forms a dark field right before the occurrence of arc to completely intercept the arc welding rays as in the first embodiment described above.

In the second embodiment, the circuit elements 16', 62, 64, 48, 50 and 52 may be mounted together on the eye-protector. Such construction allows a magnetic field generated from the cable 34 to be effectively caught by the magnetic field detector 16' mounted on the eye-protector, because this allows the eye-protector to be at a distance below 1 m in the welding operation.

Thus, in the second embodiment, elements or components which have been conventionally used in the art except the eye-protector may be used to fully interrupt arc welding rays, accordingly, the embodiment is widely applicable to various types of arc welding.

The first and second embodiments described above each are constructed to cause a bright field to be obtained when the controller carries out the on-control of a voltage applied to the PLZT filter plate 50. However, the present invention may be constructed to obtain a dark field upon the on-control of the voltage. This is accomplished by, for example, deflecting the direction of polarization of a polarizing plate such as a right-angle polarizing plate used in combination with the PLZT filter plate 50.

As can be seen from the foregoing, the present invention is adapted to detect a transient built-up current in a welding current to carry out the on-off control of the filter plate exhibiting an electro-optic effect. Accordingly, it can allow even a filter plate of a relatively slow response time such as liquid crystal or the like to be effectively actuated right before the occurrence of arc welding rays. Thus, the present invention is capable of fully intercepting welding rays generated in arc welding to effectively prevent the occurrence of an optic disease due to the arc welding rays.

Also, the present invention substantially reduces the manufacturing costs of the eye-protecting apparatus, because it does not require the use of a high quality material of a high response speed for the filter plate.

Furthermore, in the present invention, signals for the on-off control of the filter plate are obtained by not utilizing voltage drop due to the on-off of a welding current but converting the detected on and off signals of a welding current into signals different in frequency or digital signals; thus, the control of a voltage applied to the PLZT filter plate is positively carried out without malfunction, so that the filter plate may be precisely and stably operated.

While preferred embodiments of the invention have been described with a certain degree of particularity with reference to the drawings, obvious modifications and variations are possible in the light of the above teachings. It is therefore to be understood that within the scope of the appended claims, the invention may be practiced otherwise than as specifically described.

What is claimed is:

1. A method of protecting eyes against arc in welding which utilizes a personal eye-protector having a filter plate formed of a material capable of exhibiting an electro-optic effect and arranged thereon, comprising the steps of:

detecting a magnetic field generated around a welding current cable to detect the occurrence of a transient built-up current in a welding current and generating a detection signal; and controlling a voltage applied to said filter plate depending upon said detection signal;

occurrence of said magnetic field being detected by a magnetic field detector provided on an electrode holder; and said detection signal being converted into a light signal or wave signal of a predetermined frequency and being received by a receiver provided at a position of said eye-protector.

2. A method as defined in claim 1, wherein said filter plate is formed of a PLZT material.

3. The method of claim 1, wherein said filter plate responds after detection of the transient built-up current, in a period of time which is less than a delay time from occurrence of the transient built-up current to occurrence of arc discharge.

4. The method of claim 1, wherein said predetermined frequency is about 50 kHz. when no transient built-up current is detected, and about 38.4 kHz. when the transient built-up current is detected.

5. The method of claim 4, comprising the additional step of closing said filter plate when neither the frequency of 50 kHz. nor the frequency of 38.4 kHz. is received by said receiver.

6. The method of claim 1, comprising the additional step of
   discriminating said predetermined frequency from a plurality of frequencies,
   whereby the voltage applied to said filter plate depends upon the thus-discriminated frequency.

7. An eye-protecting apparatus for arc welding, comprising:
   a filter plate for an eye-protector, said filter plate being formed of a material which is capable of exhibiting an electro-optic effect;
   a power source for said filter plate which generates a voltage applied to said filter plate;
   a detection circuit for detecting a transient built-up current in a welding current;
   said detection circuit comprising a magnetic field detector, a transmitter for transmitting a plurality of signals different in frequency from each other depending upon signals supplied from said magnetic field detector thereto, a receiver for receiving the signals supplied from said transmitter, and a frequency discriminator for discriminating the frequencies of the signals received by said receiver; and
   a controller for controlling said voltage applied to said filter plate depending upon a signal supplied from said detection circuit.

8. An eye-protecting apparatus as defined in claim 7, wherein said magnetic field detector and transmitter are arranged on an electrode holder, and said frequency discriminator, said source circuit for said filter plate and said controller are arranged on said eye-protector.

9. An eye-protecting apparatus as defined in claim 8, wherein said filter plate is formed of a PLZT material.

10. An eye-protecting apparatus as defined in dlaim 7, wherein said filter plate is formed of a PLZT material.

11. The apparatus of claim 7, additionally comprising
    a light-emitter connected to said transmitter and controlled by a signal supplied from said transmitter to emit a light signal of a predetermined frequency, and
    a light receptor for receiving said light signal and connected to said receiver.

12. The apparatus of claim 11, wherein said light emitter is an infra-red light emitting diode and said light receiver is an infra-red light receiving diode.

13. The apparatus of claim 7, wherein said apparatus has a response time, from detection of the transient built-up current to response of the filter plate, less than a delay time from occurrence of the transient built-up current to occurrence of arc discharge.

14. The apparatus of claim 13, wherein said response time is a sum of a response time of said detection circuit and a response time of said filter plate.

* * * * *